United States Patent
Cohen et al.

(10) Patent No.: US 6,309,847 B1
(45) Date of Patent: *Oct. 30, 2001

(54) METHOD FOR DETECTING OR MONITORING THE EFFECTIVENESS OF TREATMENT OF T CELL MEDIATED DISEASES

(75) Inventors: Irun R. Cohen; Dana Elias, both of Rehovot (IL)

(73) Assignee: Yeda Research and Development Co. Ltd., Rehovot (IL)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/973,782
(22) PCT Filed: Jul. 2, 1996
(86) PCT No.: PCT/US96/11374
  § 371 Date: Jul. 22, 1996
  § 102(e) Date: Jul. 22, 1996
(87) PCT Pub. No.: WO97/02052
  PCT Pub. Date: Jan. 23, 1997

(30) Foreign Application Priority Data

Jul. 5, 1995 (IL) .................................................. 114459

(51) Int. Cl.⁷ ............................ A61K 49/00; G01N 33/53
(52) U.S. Cl. ........................ 435/7.24; 424/9.2; 435/7.94; 436/506
(58) Field of Search ............................... 424/9.2; 435/7.24, 435/7.94, 7.98; 436/506

(56) References Cited

U.S. PATENT DOCUMENTS 5,658,744 * 8/1997 Ochoa et al. ..................... 435/7.24

OTHER PUBLICATIONS

Burstein et al, J. Exp. Med., 177, 457–463, 1993.*
De Wit et al, J. Exp. Med., 175, 9–14, 1992.*
Secrist et al, J. Exp. Med., 178, 2123–2130, 1993.*
Allen et al, Immunology Today, 18, 387–392, 1997.*
Liblau et al, Immunology Today, 16, 34–38, 1995.*
McFarland, Science, 274, 2037–2038, 1996.*
Harrison, Leonard C., "Islet cell antigens in insulin–dependent diabetes: Pandora's box revisited.", Immunology Today, vol. 13, pp. 348–352 (1992).
Kaufman, Daniel et al., "Spontaneous loss of T–cell tolerance to glutamic acid decarboxylase in murine insulin–dependent diabetes.", Nature, vol. 366, pp. 69–72 (1993).
Tisch, Roland et al., "Immune response to glutamic acid decarboxylase correlates with insulitis in non–obese diabetic mice.", Nature, vol. 366, pp. 72–75 (1993).
Bowman, Mark A. et al., "Prevention of diabetes in the NOD mouse: implications for therapeutic intervention in human disease.", Immunology, vol. 15, No. 3, pp. 115–120 (1994).
Elias, Dana et al., "Vaccination against autoimmune mouse diabetes with a T–cell epitope of the human 65–kDa heat shock protein.", Proc. Natl. Acad. Sci. USA, vol. 88, pp. 3088–3091 (1991).
Elias, Dana et al., "Peptide therapy for diabetes in NOD mice.", The Lancet, vol. 343, pp. 704–706 (1994).
Pennline, Kenneth et al., "Recombinant human il–10 prevents the onset of diabetes in the nonobese diabetic mouse.", Clinical Immunology and Immunopathology, vol. 72, No. 2, pp. 169–175 (1994).
Weiner, Howard L., "Oral tolerance: Immunologic mechanisms and treatment of animal and human organ–specific autoimmune diseases by oral administration of autoantigens.", Annu. Rev. Immunol., pp. 809–837 (1994).
Rabinovitch, Alex., "Immunoregulatory and cytokine imbalances in the pathogenesis of IDDM.", Perspectives in Diabetes, vol. 43, pp. 613–621 (1994).
Solimena, Michele et al., "From TH1 to TH2: diabetes immunotherapy shifts gears.", Nature Medicine, vol. 2, No. 12, pp. 1311–1312 (1996).

* cited by examiner

*Primary Examiner*—David Saunders
(74) *Attorney, Agent, or Firm*—Winston & Strawn

(57) ABSTRACT

It has been discovered that treatment of an IDDM model with the p277 auto-antigen in a tolerogenic carrier induces a shift from a TH1 T cell response to a TH2 T cell response. The efficacy of proposed vaccines for any T cell mediated disease can be detected or monitored by measuring for such a TH1→TH2 T cell reponse shift.

3 Claims, 6 Drawing Sheets

METHOD FOR DETECTING OR MONITORING THE EFFECTIVENESS OF TREATMENT OF T CELL MEDIATED DISEASES

FIELD OF THE INVENTION

The present invention relates to methods for the treatment of T cell mediated diseases, such as Type I diabetes, also known as insulin-dependent diabetes mellitus (IDDM), and to methods for detecting and/or monitoring the effectiveness of such treatment.

BACKGROUND OF THE INVENTION

Type I diabetes, or IDDM, is an autoimmune disease caused by T cells that attack and destroy the insulin-producing cells located in the islets of the pancreas (Castano and Eisenbarth, 1990). The autoimmune process culminating in IDDM begins and progresses without symptoms. The disease surfaces clinically only when the cumulative loss of β-cells exceeds the capacity of the residual β-cells to supply insulin. Indeed, the collapse of glucose homeostasis and clinical IDDM is thought to occur only after 80–90% of the β-cells have been inactivated by the immune system. Thus, patients who can be identified as suffering from IDDM are bound to be in an advanced stage of autoimmune destruction of their β-cells. Moreover, diagnosis of incipient, pre-clinical diabetes by the detection of immunological markers of β-cell autoimmunity can be made only after the onset of the autoimmune process. Therefore, the therapeutic quest is to find a safe, specific and effective way to turn off an autoimmune process that is already well underway.

The present inventors have examined this question before by studying the spontaneous diabetes developing in mice of the NOD strain, which is considered to be a faithful model of human IDDM (Castano and Eisenbarth, 1990). The spontaneous autoimmune process resulting in diabetes in the NOD mouse is first detectable as a mild insulitis beginning at about 1 month of age. In most female mice, the insulitis progresses towards a penetrating intra-islet infiltrate that leads to β-cell damage and overt insulin-dependent diabetes mellitus (IDDM) that surfaces at about 4–5 months of age, (Bach, 1991). The insulitis is associated with T-cell autoreactivity and autoantibodies to a variety of self-antigens (Harrison, 1992). It has been assumed that one of the autoantigens is the primary target for an insulitis which could activate autoimmunity to additional, secondary self-antigens. The T-cell response to glutamic acid decarboxylase (GAD) was reported to be detectable before the T-cell responses to hsp60 and to other antigens (Kaufman et al., 1993; Tisch et al., 1993) and the administration of GAD by intrathymic injection at 3 days of age (Kaufman et al., 1993), or by intravenous injection at 3 weeks of age (Tisch et al., 1993), was found to inhibit the development of T-cell reactivity to the other self-antigens, including hsp60, and to prevent diabetes. The investigators concluded that autoimmunity to GAD might be the primary event leading to diabetes. However, a variety of seemingly "non-specific" manipulations applied early in the course of insulitis can prevent or delay the later development of diabetes (Bowman et al., 1994).

In addition to the GAD antigen, autoimmunity to hsp60 has been shown to have a functional role in NOD diabetes (PCT Patent Publication No. WO 90/10449): T cells responsive to the hsp60 peptide p277 could adoptively transfer diabetes or, when attenuated, could vaccinate mice against diabetes (Elias et al., 1991); and a single, subcutaneous administration of peptide p277 in oil either early (Elias et al., 1991) or very late in the autoimmune process (Elias et al., 1994) could arrest the disease.

T cells of the CD4 "helper" type have been divided into two groups by the characteristic cytokines they secrete when activated (Mosmann et al., 1989). TH1 cells secrete IL-2, which induces T-cell proliferation, and cytokines such as IFNγ, which mediate tissue inflammation; TH2 cells, in contrast, secrete IL-4 and IL-10. IL-4 helps β-cells secrete antibodies of certain IgG isotypes and suppresses the production of TH1 inflammatory cytokines (Banchereau et al., 1994). IL-10 indirectly inhibits TH1 activation by affecting antigen-presentation and inflammatory cytokine production by macrophages (Moore et al., 1993).

It has now been discovered by the laboratory of the present inventors that the successful treatment of the autoimmune process in IDDM by administration of the peptide p277 in oil is caused by the effect of this treatment in aborting TH1-type autoimmunity to several different antigens and instead activating p277 autoimmunity into a TH2 mode. Thus, a disease with a spectrum of autoreactivities can be turned off with a single peptide capable of inducing a T cell cytokine shift.

SUMMARY OF THE INVENTION

It is an object of the present invention to determine or monitor the effectiveness of treatment of a T cell mediated disease by means of testing, in an appropriate animal model, for a shift from a TH1 cell response to a TH2 T cell response over time. This may be accomplished by detecting a shift in the antibody isotype from IgG2a to IgG1 and IgG2b isotype antibodies, or detecting a shift from the proliferation of the cytokines from IL-2 and IFNγ to IL-4 and IL-10.

It is a further object of the present invention to determine optimum vaccine dosages and regimens by measuring for an optimal shift from a TH1 T cell cytokine response to a TH2 T cell cytokine response.

BRIEF DESCRIPTION OF THE DRAWINGS

FIG. 3A shows the results of an assay for the isotypes of the antibodies of NOD mice to intact hsp60 (closed circles) or to GAD (open circles) prior to treatment. Control sera from BALB/c mice are indicated by x.

FIG. 4A shows the amount of IL-2 secreted after 24 hours of incubation; FIG. 4B shows the amount of IFN$\gamma$ secreted after 48 hours of incubation; FIG. 4C shows the amount of IL-10 secreted after 48 hours of incubation; and FIG. 4D shows the amount of IL-4 secreted after 24 hours of incubation. An asterisk indicates $p<0.01$ by Student's T test.

DETAILED DESCRIPTION OF PREFERRED EMBODIMENTS

Figure 1:
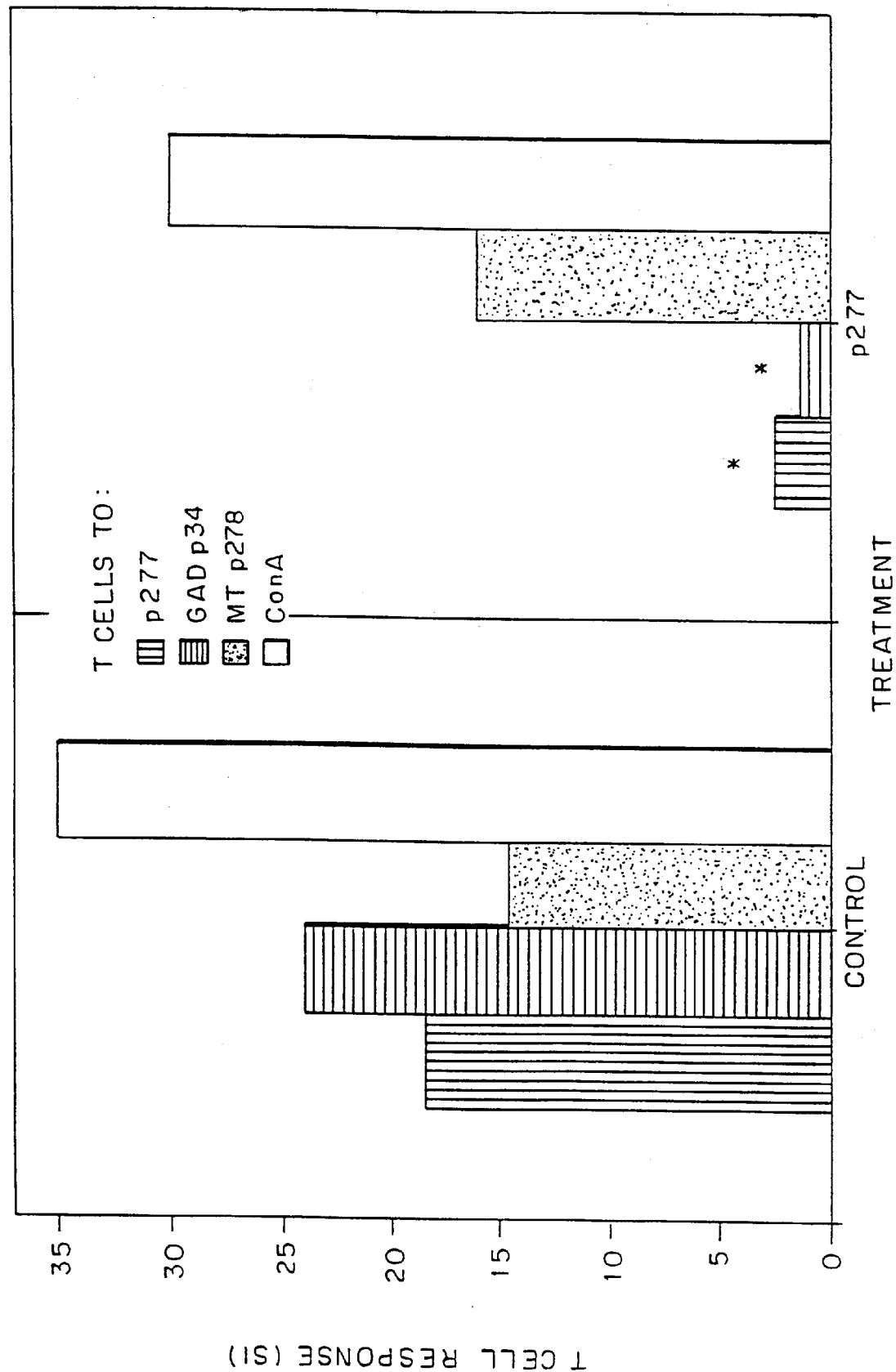
FIG. 1 contains graphs showing that the T cell proliferative responses to GAD and hsp60 peptides are specifically reduced by p277 therapy. In the right panel, NOD mice were treated with peptide p277 emulsified in mineral oil and in the left panel, the NOD mice were treated with phosphate buffered saline (PBS) emulsified in mineral oil. The various bars of the graph show the T cell proliferative responses to the T cell mitogen Con A (open bars), p277 (vertical stripes), GAD p34 (horizontal stripes), and MT-p278 (stippled bars). The asterisks indicate p<0.01 by Student's T test.

NOD mice spontaneously develop type I diabetes caused by autoimmune T cells that attack the insulin-producing $\beta$-cells of the islets. The autoimmune attack is associated with T-cell reactivity to a variety of self-antigens including a peptide of the 60 kDa heat shock protein (hsp60) and peptides of glutamic acid&decarboxylase (GAD). The laboratory of the present inventors recently reported that the peptide of hsp60, designated p277, could be used to arrest or reverse the autoimmune process even after the development of advanced insulitis and overt diabetes. It has now been discovered that p277-peptide treatment down-regulates the spontaneous T-cell proliferative responses to epitopes of both hsp60 and GAD and abolishes the production of autoantibodies to hsp60, to GAD and to insulin. Arrest of the disease process is associated, not with T-cell tolerance or anergy, but with a shift in the cytokines produced by the autoimmune T cells reactive to p277 from a TH1-like profile (IL-2, IFN$\gamma$) to a TH2-like profile (IL-4, IL-10). The modulation is immunologically specific; the spontaneous T-cell response of the treated mice to a bacterial hsp60 peptide remains in the TH1 mode. Thus, the diabetogenic process characterized by autoimmunity to several self antigens can be cured using one of the antigens, peptide p277.

This discovery that a disease with a spectrum of autoreactivities can be turned off with a single peptide capable of inducing a T cell cytokine shift leads to the present invention which provides a new tool for finding peptides capable of regulating destructive autoimmunity and whose principle is broadly applicable to any autoimmune disease and, indeed, any disease mediated by T cell activity and particularly TH1 cell activity.

The methods of the present invention all involve detection of or monitoring of a shift from a TH1 T cell response, which is almost universally found in organ-specific autoimmune diseases, to a TH2 T cell cytokine response over a period of time. It is not important whether this cytokine shift reflects a relative increase in the TH2 cells responsive to the vaccinating peptide or whether clones of anti-antigen cells of the TH1 type change their behavior at the clonal level. While applicants do not wish to be limited to any particular theory, it is believed that it is more likely that the antigen which causes such a shift induces the production of TH2 cells and that the cytokines produced by such predominating TH2 cells cause a suppression of the existing TH1 cells which caused the inflammatory attack.

In either case, any treatment modality which causes such a shift in an animal suffering from an autoimmune disease will be a preferred treatment modality. The detection of such capability or the monitoring of the effect of any such peptide on a given autoimmune disease can readily be accomplished by means of the present invention by administering the proposed treatment modality to an animal having an autoimmune disease or other T cell mediated inflammatory condition, preferably an accepted laboratory model of a human autoimmune disease, and then testing the treated animals for the signs of a shift from a TH1 T cell response to a TH2 T cell response.

The existence and the degree of TH1→TH2 shift serves as evidence that the treatment was effective and did induce a beneficial response. In other words, the TH1→TH2 shift can serve as a surrogate marker of the response to treatment. For example, the lack of the shift can indicate a need for a second treatment.

Examples of markers of such a response shift include the determination of the antibody response induced by the T cells or a determination of the cytokines being produced by the T cells. For example, it is known that TH1 type T cells induce the production of antibodies of the IgG2a class, while TH2 type antibodies induce the production of antibodies of the IgG1 and IgG2b class. Thus, by assaying for the isotype of antibodies to the administered antigen before and after treatment, one can monitor the extent of the shift from a TH-1 T cell response to a TH2 T cell response.

Similarly, it is known that TH1 cells secrete IL-2, which induces T cell proliferation, and cytokines such as IFN$\gamma$, which mediate tissue inflammation. On the other hand, TH2 cells secrete IL-4, which helps $\beta$-cells secrete antibodies of the IgG1 and IgG2b class and suppresses the production of TH1 inflammatory cytokines, as well as IL-10, which indirectly inhibits TH1 activation by affecting antigen presentation and inflammatory cytokine production by macrophages. Accordingly, a measurement of the cytokine profile of the T cells of treated animals will also be an indication of a shift from a TH1 T cell response to a TH2 T cell response. Thus, for example, spleen cells from treated animals can be removed and incubated with the antigen which had been administered to induce the secretion of cytokines. The cytokines in the culture supernatants can then be quantitated, for example by ELISA using the standard cytokine ELISA protocols.

Modalities for the treatment of any autoimmune disease or other T cell mediated diseases or conditions may be detected or monitored in accordance with the present invention, which diseases include but are not limited to IDDM, multiple sclerosis, myasthenia gravis, scleroderma, polymyositis, graft-versus-host disease, graft rejection, Graves disease, Addison's disease, autoimmune uveoretinitis, autoimmune thyroiditis, pemphigus vulgaris, rheumatoid arthritis, ankylosing spondylitis, T cell mediated allergic response, etc. Preferably, however, such disease is one which is TH1 cell mediated.

Known and accepted animal models for many of these diseases are readily available. These include, for example, NOD mice as a diabetes model, mice with experimentally induced experimental autoimmune encephalomyelitis (EAE) as a multiple sclerosis model, mice with experimental autoimmune thyroiditis (EAT) as a model for autoimmune thyroiditis, mice with adjuvant arthritis (AA) as a model for rheumatoid arthritis, etc.

Vaccines comprising the suspected auto-antigen must be administered in a tolerogenic carrier in order to avoid further exacerbating the autoimmune process. Such carriers include mineral oil carriers such as incomplete, Freund's adjuvant (IFA) or complete Freund's adjuvant (CFA). IFA is an emulsion of mineral oil. CFA is a preparation of mineral oil containing various amounts of killed organisms of Mycobacterium. However, IFA and CFA are not allowed for human use because the mineral oil is not metabolizable and cannot be degraded by the body. It has recently been found that certain fat emulsions, which have been in use for many years for intravenous nutrition of human patients, can also act as a vehicle for peptide therapy using the peptides of the present invention. Two examples of such emulsions are the available commercial fat emulsions known as Intralipid and Lipofundin. "Intralipid" is a registered trademark of Kabi Pharmacia, Sweden, for a fat emulsion for intravenous nutrition, described in U.S. Pat. No. 3,169,094. "Lipofundin" is a registered trademark of B. Braun Melsungen, Germany. Both contain soybean oil as fat (100 or 200 g in 1,000 ml distilled water: 10% or 20%, respectively). Egg-yolk phospholipids are used as emulsifiers in Intralipid (12 g/l distilled water) and egg-yolk lecithin in Lipofundin (12 g/l distilled water). Isotonicity results from the addition of glycerol (25 g/l) both in Intralipid and Lipofundin.

It is believed that these vehicles are actually biologically active carriers which when complexed with the suspected auto-antigen, promote the TH1→TH2 shift of the autoimmune T cells. Thus, it is preferred to use such vehicles when testing for possible auto-antigens for human use. Such a vehicle is preferably a fat emulsion comprising 10–20% triglycerides of plant and/or animal origin, 1.2–2.4% phospholipids of plant and/or animal origin, 2.25–4.5% osmoregulator, 0–0.05% anti-oxidant, and sterile water to 100%. Such vehicle is most preferably Intralipid or Lipofundin. Use of such vehicles is described in an Israeli patent application (identified by applicant's reference 9523) filed on even date with the date of filing of the original Israeli application on the present invention (identified by applicant's reference 9536), with the same applicant (assignee) as the present application, the entire contents of which are hereby incorporated herein by reference.

The method of the present invention, however, is independent of the particular adjuvant used and any antigen-adjuvant complex may be tested by means of the present invention. If the T cell response to the auto-antigen in an experimental animal model is shifted from a TH1 to a TH2 response, as determined by means of the test of the present invention, then one has identified a potentially useful modality for the treatment of the corresponding human disease.

The method of the present invention can also be used to screen for tolerogenic adjuvants which have the biological effect of mediating a TH1→TH2 shift when administered in combination with or complexed with an antigen recognized by the inflammatory TH1 cells associated with the pathogenesis of the disease or condition to be treated. Thus, for example, it is known that when p277 is combined with an appropriate antigen a TH1→TH2 shift can be detected by the means disclosed in the present examples. In order to screen other adjuvants for the capability of mediating such a TH1→TH2 shift in combination with p277, such proposed adjuvants can be substituted for the mineral oil or Intralipid of the present examples and the presence of a TH1→TH2 shift measured. If such a shift is found, then the adjuvant can be classified as a biologically active tolerogenic adjuvant which can be used, in combination with an antigen recognized by the TH1 cells associated with the pathogenesis of any TH1-mediated disease, in a vaccine for the treatment of patients suffering from such disease. Any such adjuvant found using the process of the present invention is considered to be part of the present invention. Any other antigen known to mediate a TH1→TH2 shift when administered with mineral oil or Intralipid, can also be used for the purpose of this test.

The shift should be measured over an appropriate period of time such as, for example, 2–12 weeks after administration of the vaccine. The efficacy of the treatment may be monitored over a longer period of time by periodically testing for the relative TH1→TH2 cytokine response.

Specific techniques for assaying the isotype of antibodies and for assaying the presence of various cytokines are not per se a novel part of the present invention. Those of ordinary skill in the art are well aware of various manners of assaying for antibody isotype or for the various cytokines produced by TH1 and TH2 T cells. Any such technique can be used in the course of the present invention for detecting a TH1 to TH2 shift. The examples presented herein disclose illustrative manners of doing so, but it is not intended that the present invention be limited thereto. For example, rather than using spleen cells, peripheral circulating T cells can be obtained from the patient and tested for cytokine response.

EXAMPLES

Example 1

Specific Reduction of Spontaneous T Cell Proliferative Responses to GAD and hsp60 Peptides by p277 Therapy The present experiment was conducted to determine the immunologic mechanism associated with cure of the autoimmune process by p277 therapy. 133 female NOD/Lt mice, at age 12 weeks with advanced insulitis (Elias et al., 1994), were treated either with p277 emulsified in mineral oil (IFA purchased from Difco, Detroit, Mich.) (81 mice) or with control phosphate buffered saline (PBS) emulsified in mineral oil (52 mice) as described in Elias et al., 1994. Almost all control-treated mice developed diabetes (92%) and most died of uncontrolled hyperglycemia (58%) by 25 weeks of age (Elias et al., 1994). In contrast, only 28% of the p277-treated mice developed diabetes and only 17% died (p<0.01). Spleen cells were obtained from parallel groups of mice and tested at 17 weeks of age (5 weeks after treatment) for their T-cell proliferative responses assayed in vitro to peptide p277 of hsp60 (10 µg/ml), to peptide p34 of GAD (Kaufman et al., 1993) (10 µg/ml) or to peptide MT-p278 of Mycobacterial hsp60 (10 µg/ml) using a standard assay (Elias et al., 1991). The NOD mice of the inventors' laboratory show spontaneous T-cell reactivity to peptide MT-p278, so this peptide serves as a convenient T-cell specificity control. T-cell cultures also were activated with the T-cell mitogen Con A (1.25 µg/ml).

The peptides were synthesized by standard Fmoc using a automated ABIMED synthesizer (Germany) as described (Elias et al., 1994). The peptides were purified by reverse phase HPLC and their compositions were confirmed by amino acid analysis. The sequence of GAD peptide 34 (residues 509–528; GADp34) was Ile-Pro-Pro-Ser-Leu-Arg-Thr-Leu-Glu-Asp-Asn-Glu-Glu-Arg-Met-Ser-Arg-Leu-Ser- Lys (SEQ ID NO:1) (Kaufman et al., 1993). The sequence of MT-p278 was Glu-Gly-Asp-Glu-Ala-Thr-Gly-Ala-Asn-Ile-Val-Lys-Val-Ala-Leu-Glu-Ala (SEQ ID NO:2). The sequence of p277 used in all of the experiments reported in the present specification was Val-Leu-Gly-Gly-Gly-Val-Ala-Leu-Leu-Arg-Val-Ile-Pro-Ala-Leu-Asp-Ser-Leu-Thr-Pro-Ala-Asn-Glu-Asp (SEQ ID NO:3). This peptide is substituted at positions 6 and 11 with valine (Val) in place of the cysteine (Cys) in the native sequence. Substitution of the two Cys residues by Val enhances greatly the stability of the peptide without affecting its immunological activity. The Val-substituted peptide is completely cross-reactive with the native peptide by T-cell and antibody assays, and both peptides have the same therapeutic effect on diabetes. See Israeli application 112,091 filed Dec. 21, 1994, and a second Israeli application, identified by applicant's reference 9451A, filed on even date with the date of filing of the original Israeli application on the present invention (identified by applicant's reference 9536), both of which are hereby incorporated herein by reference in their entirety. All the effects shown in this paper have been repeated with either variant of p277.

The T-cell responses were detected by the incorporation of [$^3$H] thymidine adder to the wells in quadruplicate cultures for the last 18 hours of a 3 day culture. The stimulation index (SI) was computed as the ratio of the mean cpm of antigen-containing wells to control wells cultured without antigens or Con A. The standard deviations from the mean cpm were always less than 10%. Background cpm, in the absence of antigens, was 800–1500 cpm.

The results, presented in FIG. 1, show that the control NOD mice that had been injected with the emulsion of PBS in oil manifested spontaneous reactivity to all 3 peptides and to Con A. Untreated control mice manifested similar spontaneous T-cell reactivities (not shown). In contrast, the p277-treated mice showed a specific fall (p<0.01) in their autoimmune T-cell proliferative responses to the hsp60 and GAD peptides; the control responses to MT-278 and to Con A remained intact. Thus, treatment with hsp60 peptide p277, which arrested the progression of diabetes, was associated with a specific decrease in the T-cell responses to both the hsp60 and GAD peptides. This decrease in autoreactivity, however, does not rule out the possibility that it is due to T-cell tolerance or anergy as opposed to some other mechanism.

Example 2

Induction of Antibodies to p277 and Reduction of Antibodies to GAD, Insulin and Intact hsp60 After Treatment with P277

In addition to T-cell reactivities, the development of diabetes in NOD mice has also been associated with the spontaneous appearance of autoantibodies to self-antigens such as hsp60 (Elias et al., 1990), GAD (Tisch et al., 1993) and insulin (Elias et al., 1990). This example studies the effects of p277 treatment on the incidence of such antibodies.

Figure 2:
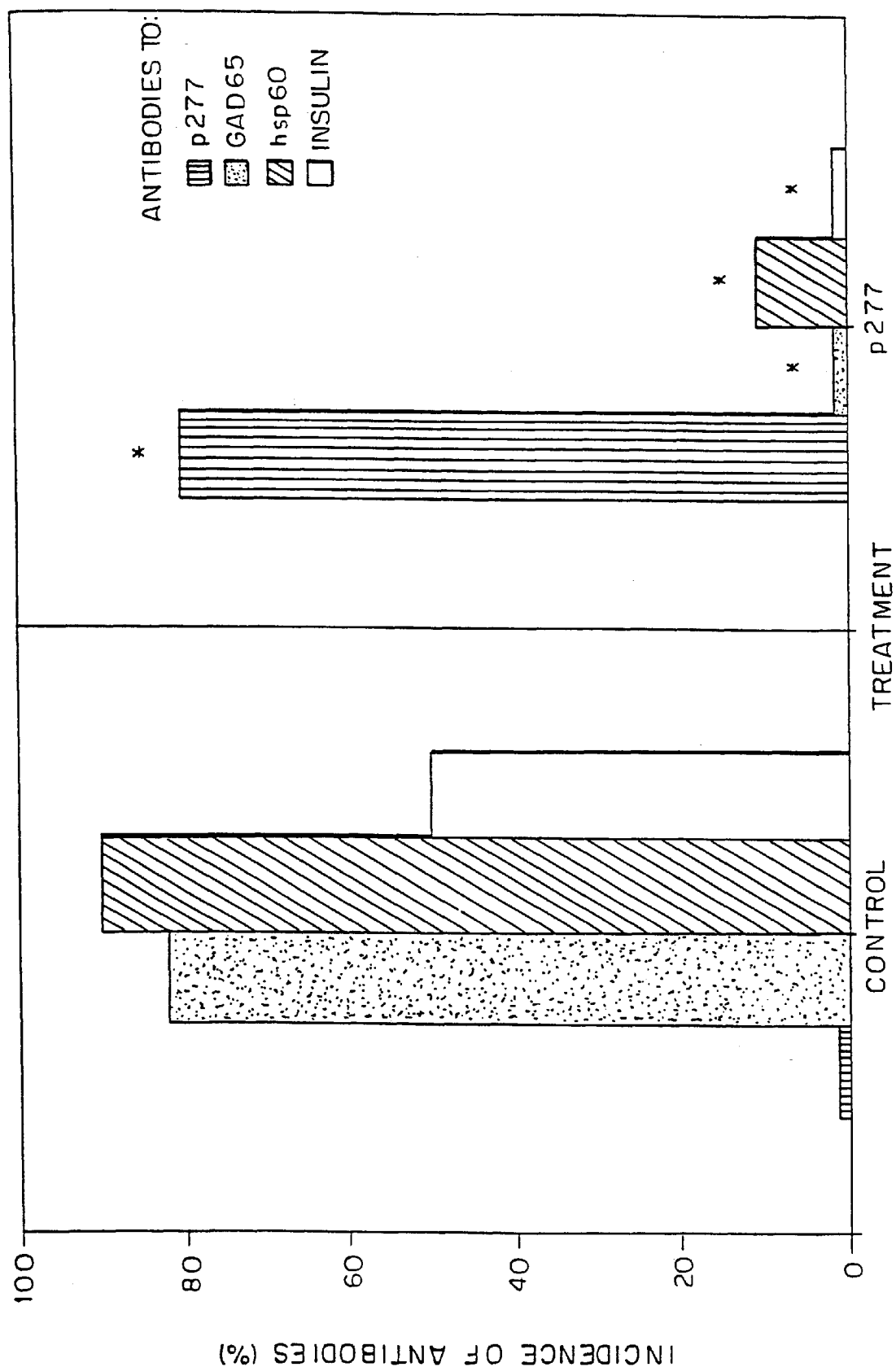
FIG. 2 is a graph showing that treatment with p277 induces antibodies to p277 and reduces antibodies to GAD, to insulin and to intact hsp60. The right panel shows the results of the treatment of NOD mice with p277 in oil and the left panel is a control in which the NOD mice are treated with PBS in oil. The bars show the percent incidence of antibodies to recombinant GAD65 (stippled bars), to recombinant human hsp60 (slanted stripes), to bovine insulin (open bars), or to peptide p277 (vertical stripes). The asterisks indicate p<0.01 by Chi Square test.

Groups of 10 NOD mice, 3 months old, were treated with p277 in oil or with PBS in oil as described in Example 1. Five weeks later, the mice were bled individually and their sera, diluted 1:50, were tested for antibodies to recombinant GAD65 (Kaufman et al., 1993), to recombinant human hsp60 (Elias et al., 1991), to bovine insulin (Sigma), or to peptide p277, in an ELISA assay as described (Elias et al., 1991). Briefly, 10 μg of the various antigens were applied to assay plates (Maxisorp Nunc plates were used as they were suitable for the binding of p277), and were incubated with the test sera. The binding of antibodies to the adherent antigens was detected using alkaline phosphatase conjugated anti-mouse IgG+IgM (Jackson ImmunoResearch Laboratories, West Grove, Pa.). A significant amount of antibody was defined as an OD 405 nm reading of greater than 0.251, which is 3 SD over the mean ELISA reading obtained in the sera of 10 normal BALB/c mice. The results are shown in FIG. 2 as the incidence of mice positive for antibodies to the various antigens. A sample of actual OD 405 nm readings can be seen in FIG. 3.

FIG. 2 shows the incidence of mice with these autoantibodies in the control-treated and p277-treated groups. It can be seen that the control-treated NOD mice manifested a high incidence of antibodies to GAD (80%) and to hsp60 (90%), and a moderate incidence of anti-insulin antibodies (50%); there were no antibodies to peptide p277. Similar results were obtained in untreated control mice (not shown). In contrast, the p277-treated mice showed a significant reduction in the incidence of autoantibodies to GAD, hsp60, and insulin (p<0.01). Thus, p277-peptide therapy of the autoimmune diabetogenic process was marked by a specific fall in the spontaneous T-cell proliferation directed to hsp60 and GAD peptides and by disappearance of the autoantibodies to GAD, hsp60 and insulin molecules. However, T-cell tolerance or anergy to p277 cannot be responsible for the decreased autoimmunity because the p277-treated mice manifested a marked increase (80%) in the incidence of antibodies to p277 (p<0.01). The association of p277 therapy with a switch in reactivity to p277 from T-cell proliferation to antibodies suggests that the therapeutic effect might result from a shift in the predominant cytokines produced by the autoimmune T cells in the treated mice.

Example 3

Analysis of Isotypes of Antibodies Produced Before and After P277 Therapy

Figure 3B:
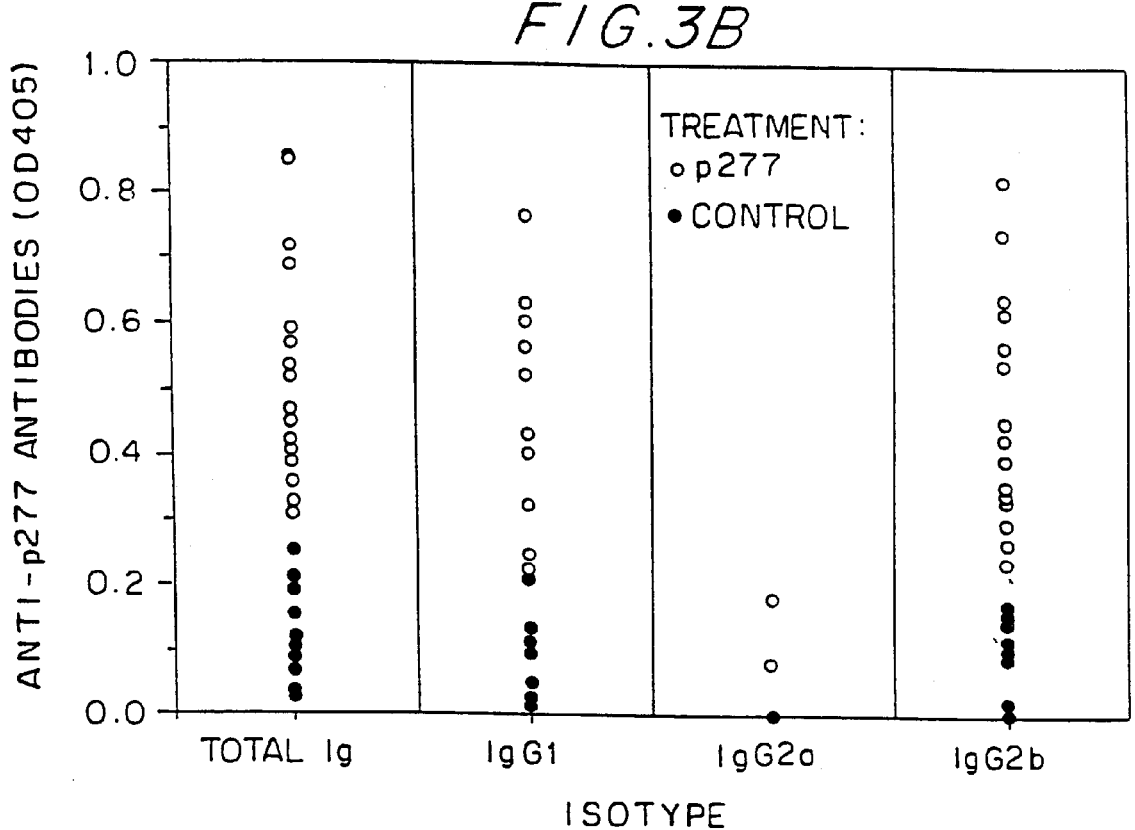
FIG. 3B shows the results of an assay for the isotype of antibodies to p277 five weeks after treatment in control-treated mice (open circles) or in p277-treated mice (closed circles). The columns in each experiment show results from equal numbers of mice; an apparent reduction in numbers of circles is caused by superimposition.
Figure 3A:
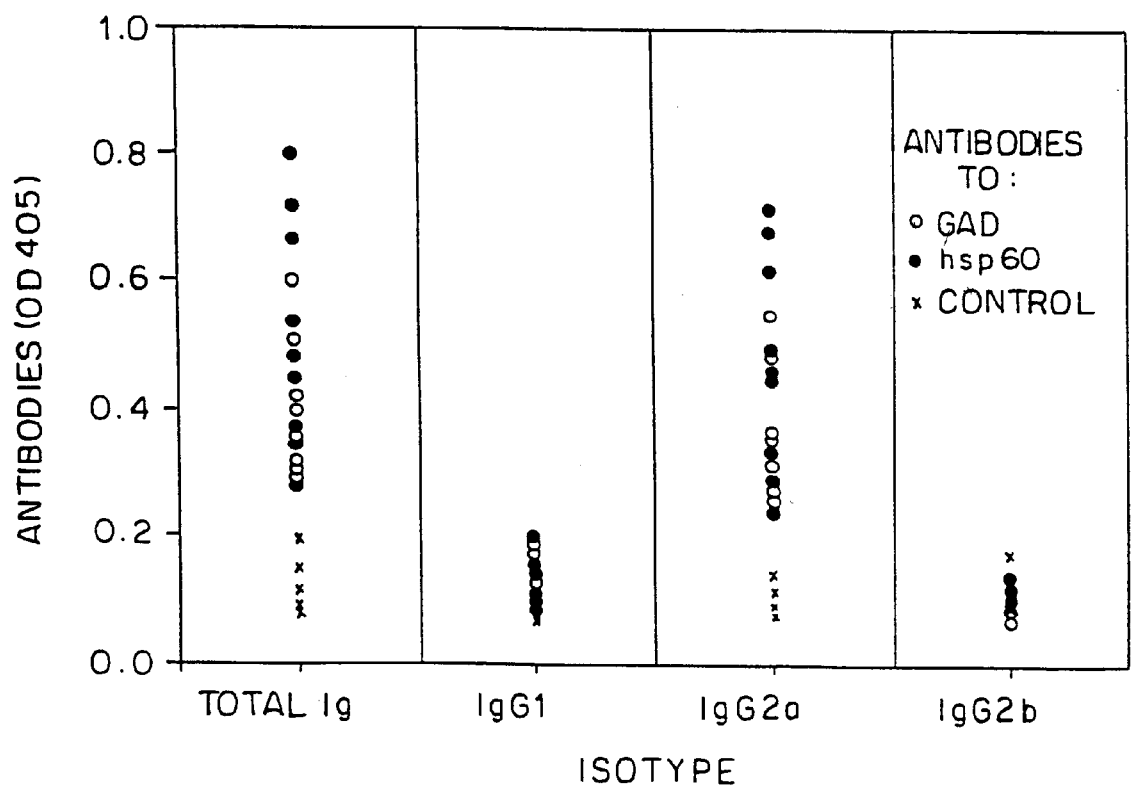
FIGS. 3A and B are graphs showing the antibody isotypes before and after p277 therapy.

The possibility of a shift from TH1 to TH2-like behavior was supported by analysis of the isotypes of the antibodies produced before and after p277 therapy. FIG. 3A shows that the spontaneous autoantibodies to GAD and to intact hsp60 present before treatment with p277 were of the IgG2a class, antibodies dependent on T cells of the TH1 type that secrete IFNγ (Snapper and Mond, 1993). These IgG2a autoantibodies disappeared within 5 weeks after treatment with p277. In contrast, analysis of the antibody isotypes of the anti-p277 antibodies developing after treatment showed them to be exclusively of the IgG1 and IgG2b classes, dependent on TH1 T cells producing IL-4 (Snapper and Mond, 1993) and possibly TGFβ (Snapper et al., 1993). There were no TH1-type IgG2a antibodies induced by p277 therapy (FIG. 3B).

Example 4

Measurement of Cytokine Profile Before and After Peptide P277 Therapy

To confirm the idea of a cytokine switch, the cytokines produced by the T-cells reactive to the p277 and MT-p278 peptides in the p277-treated and control, mice were assayed. Groups of 10 NOD mice, 3 months old, were treated with p277 in oil or with PBS in oil (see Example 1). Three weeks later, the spleens of the mice were removed and the spleen cells were pooled. The spleen cells were incubated in triplicate with Con A, p277 or MT-p278 for 24 h (for IL-2 and IL-4 secretion) or for 48 h (for IL-10 and IFNγ secretion). The presence of the cytokines in the culture supernatants was quantitated by ELISA, using Pharmingen paired antibodies according to the Pharmingen cytokine ELISA protocol. Pharmingen recombinant mouse cytokines were used as standards for calibration curves. Briefly, flat-bottom 96-well microtiter plates were coated with rat anti-mouse cytokine mAbs for 18 h at 4° C., and the culture supernatants or recombinant mouse cytokines were added for 18 h at 4° C. The plates were washed, and biotinylated rat anti-mouse cytokine mAbs were added for 45 min at room temperature, then extensively washed, and avidin-alkaline phosphatase was added for 30 min. The plates were washed, a chromogen substrate was added and samples were read at 405 nm in an ELISA reader. The concentrations of cytokines are shown as mean units/ml derived from calibration curves using recombinant cytokines as standards. The results are shown in FIGS. 4A–4D.

Figure 4A:
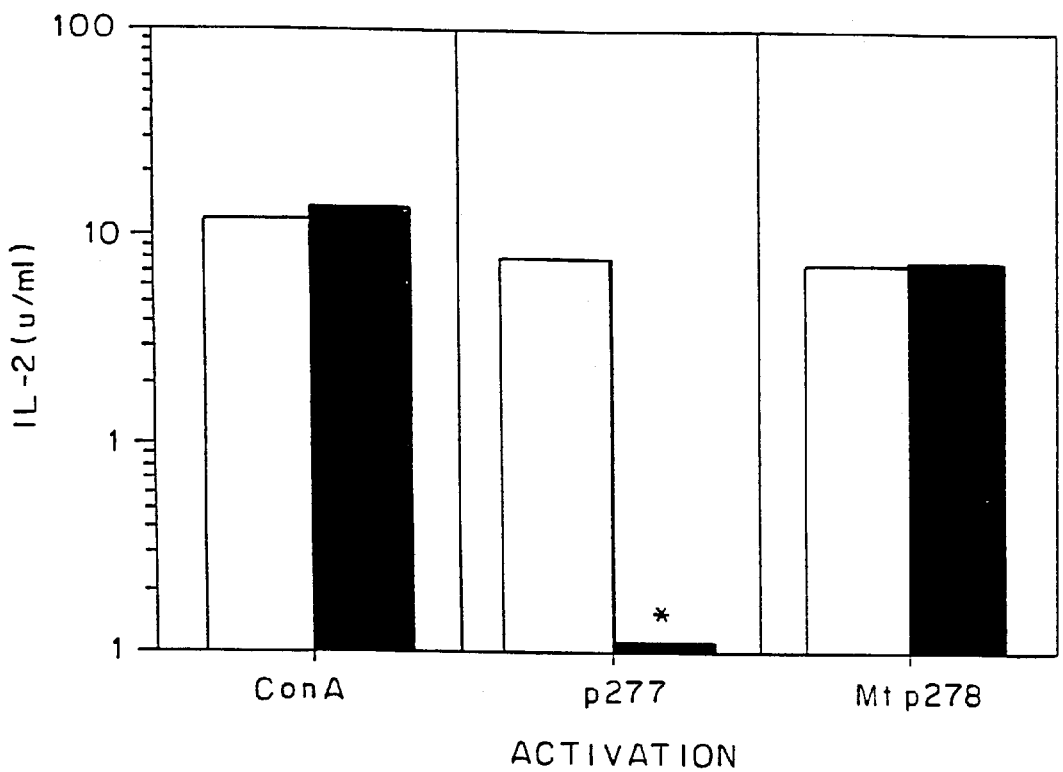
FIGS. 4A–4D are graphs showing the cytokine profile of T cells before and after p277 peptide therapy. Groups of 10NOD mice, three months old, were treated with p277 in oil (closed bars) or with PBS in oil (open bars). The amount of specific cytokines induced after incubation of spleen cells from these mice with Con A, p277 or MT p278 are shown.
Figure 4B:
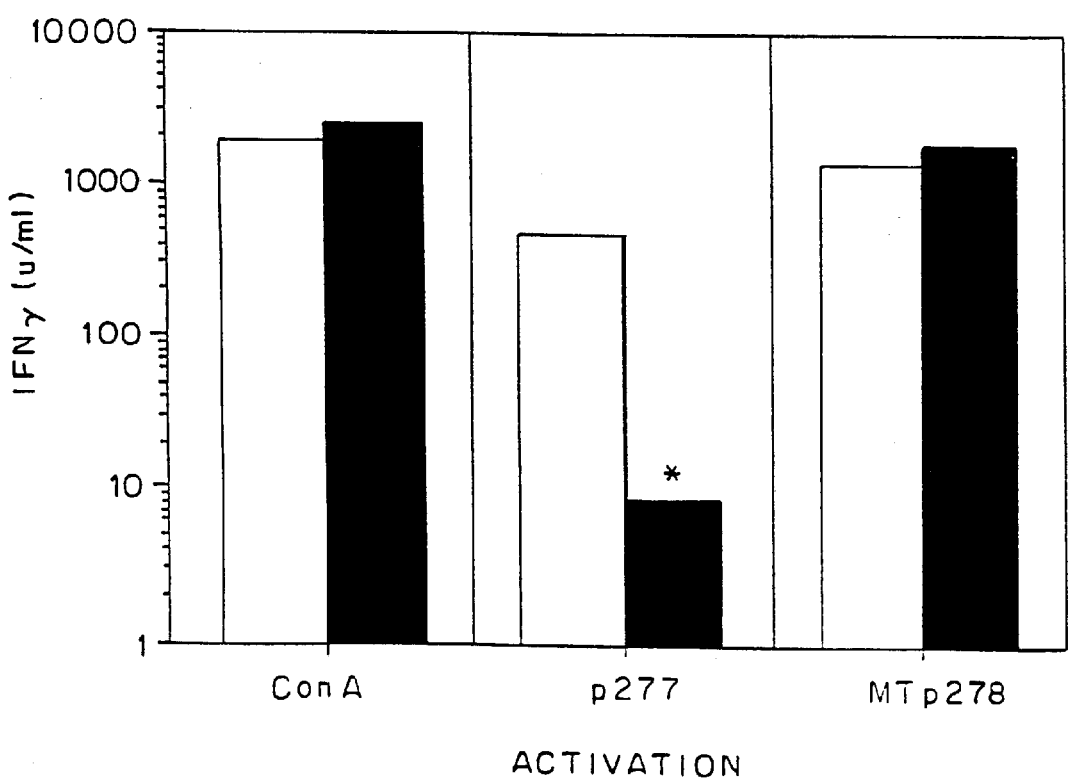
Figure 4C:
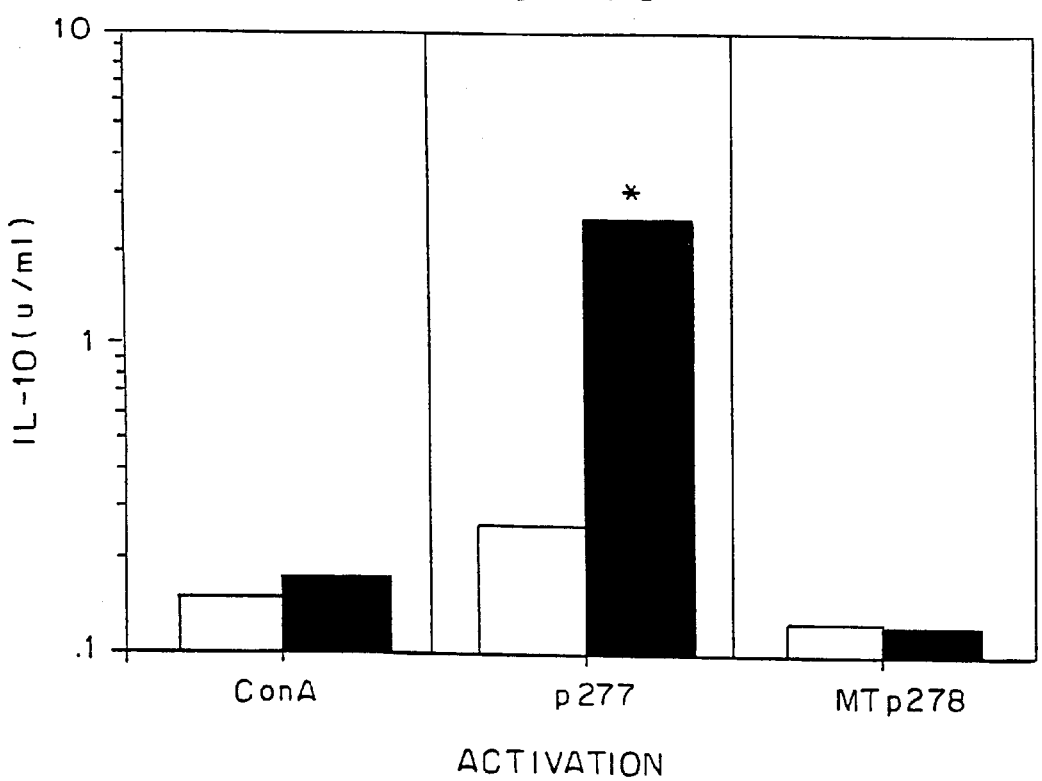
Figure 4D:
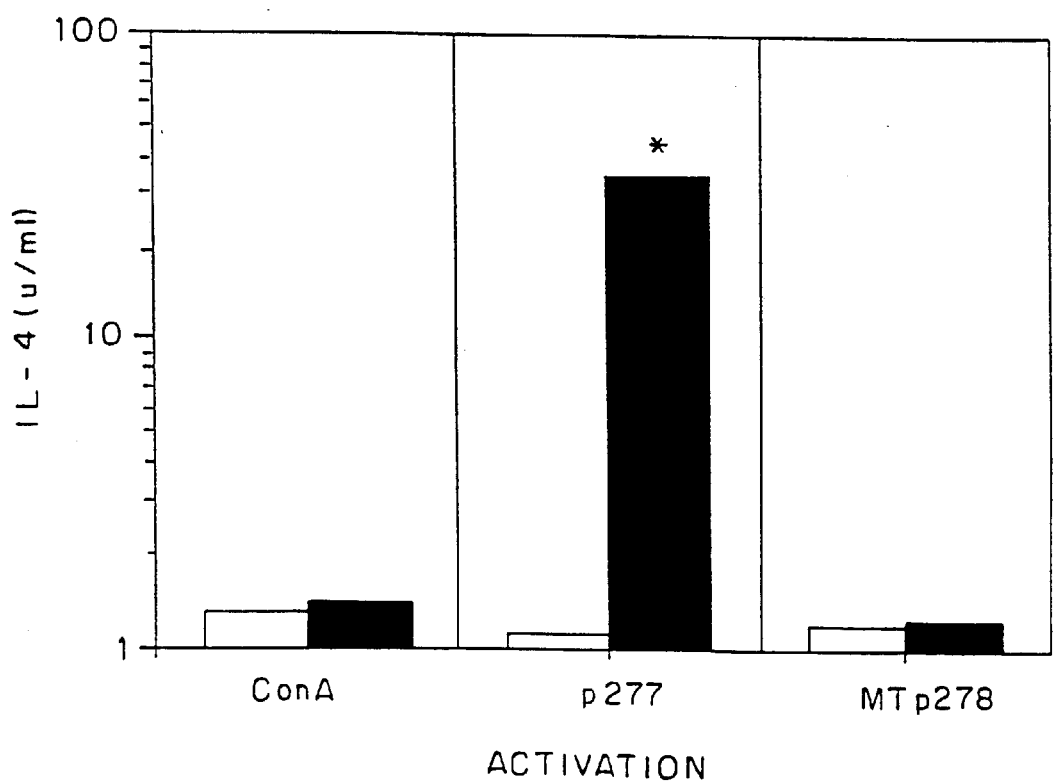

FIG. 4A and FIG. 4B show that the spleen cells of control mice secreted both IL-2 and IFNγ upon incubation with either p277, MT-p278 or the T-cell mitogen Con A. In contrast, the p277-treated mice produced significantly less ($p<0.01$) IL-2 and IFNγ in response to incubation with peptide p277. This reduction in TH1 cytokines was specific; the p277-treated mice maintained their IL-2 and TNFγ cytokine responses to MT-p278. FIG. 4C and FIG. 4D show the amounts of IL-10 and IL-4 produced by the spleen cells of the mice. The control mice produced very little IL-4 in response to p277, MT-p278 or Con A and only a small amount of IL-10 in response to p277. In contrast, there was a significant increase in IL-10 and IL-4 in response only to p277 and only in the p277-treated mice ($p<0.01$). A decrease in IL-2 and IFNγ coupled with an increase in IL-10 and IL-4 confirms the shift from TH1-like behavior to TH2-like behavior. Such a shift could explain both the decline in T-cell proliferation to p277 and the appearance of IgG1 and IgG2b antibodies to p277. Thus, the beneficial effect of p277-peptide therapy is caused not by inactivating the autoimmune response, but by activating the autoimmunity into a different cytokine mode of behavior (Cohen, 1995; Liblau et al., 1995).

Example 5

Peptide Therapy of Type I Diabetes Using p277 in Lipid Emulsions

NOD female mice were treated with 100 μg of peptide p277 per mouse subcutaneously in 0.1 ml of:

(i) Phosphate-buffered saline (PBS); and (ii) a 10% lipid emulsion composed of 10% soybean oil, 1.2% egg phospholipids and 2.25% glycerol (Intralipid, Kabi Pharmacia AB, Sweden).

The incidence of diabetes at 6 months of age and the production of anti-p277 antibodies was followed. Diabetes was diagnosed as persistent hyperglycemia, blood glucose levels over 200 mg/dl measured at least twice at weekly intervals with a Beckman Glucose Analyzer II. Successful peptide treatment was assayed by maintenance of a normal blood glucose concentration (less than 200 mg/dl), remission of the intra-islet inflammation of the pancreatic islets (insulitis) and induction of antibodies to the therapeutic peptide as an indicator of a TH2-type immune response. The results are shown in Table 1.

TABLE 4

Incidence of Diabetes at 6 months

| Treatment | Diabetes Incidence (%) | Death (%) |
|---|---|---|
| p277/PBS | 90 | 80 |
| p277/Intralipid | 45# | 20# |
| none | 100 | 90 | p < 0.01 compared to untreated NOD mice

As can be seen from Table 1, treatment with p277 administered in Intralipid was effective in reducing the incidence of diabetes and death. On the other hand, treatment administered in PBS was ineffective.

Example 6

Peptide P277/Intralipid Therapy Induces a Specific Switch in the Cytokine Profile To confirm that a TH1→TH2 cytokine switch occurs with p277 when using Intralipid as an adjuvant, the cytokines produced by the T-cells reactive to the p277 in the p277/Intralipid-treated and control mice were assayed. Concanavalin A (Con A), a T-cell mitogen, was used to activate total splenic T-cells as a control.

Figure 5A:
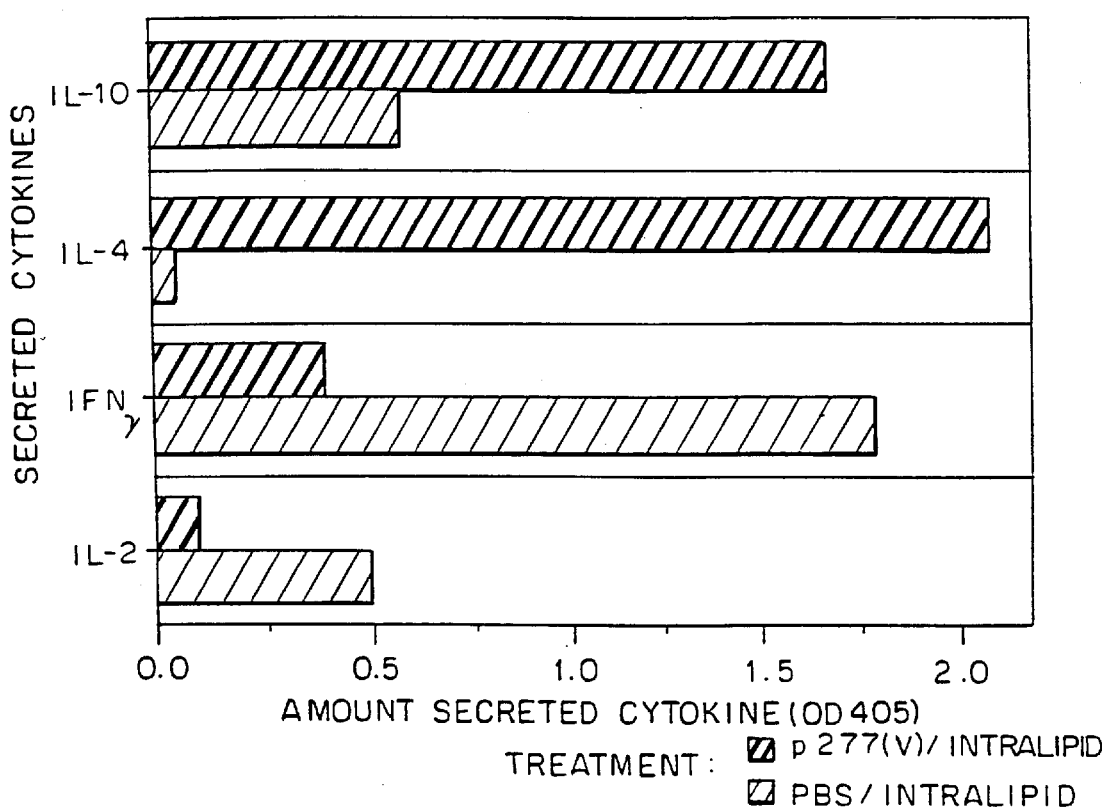
FIGS. 5A–5B are graphs showing the cytokine profile of T cells before and after p277/Intralipid peptide therapy. Groups of 10 NOD mice, three months old, were treated with p277 in Intralipid (closed bars) or with PBS in Intralipid (open bars). The amount of IL-2, IFN$\gamma$, IL-4 and IL-10 induced after incubation of spleen cells from these mice with p277 (FIG. 5A) or with Con A (FIG. 5B) are shown. The asterisk indicates $p<0.01$.
Figure 5B:
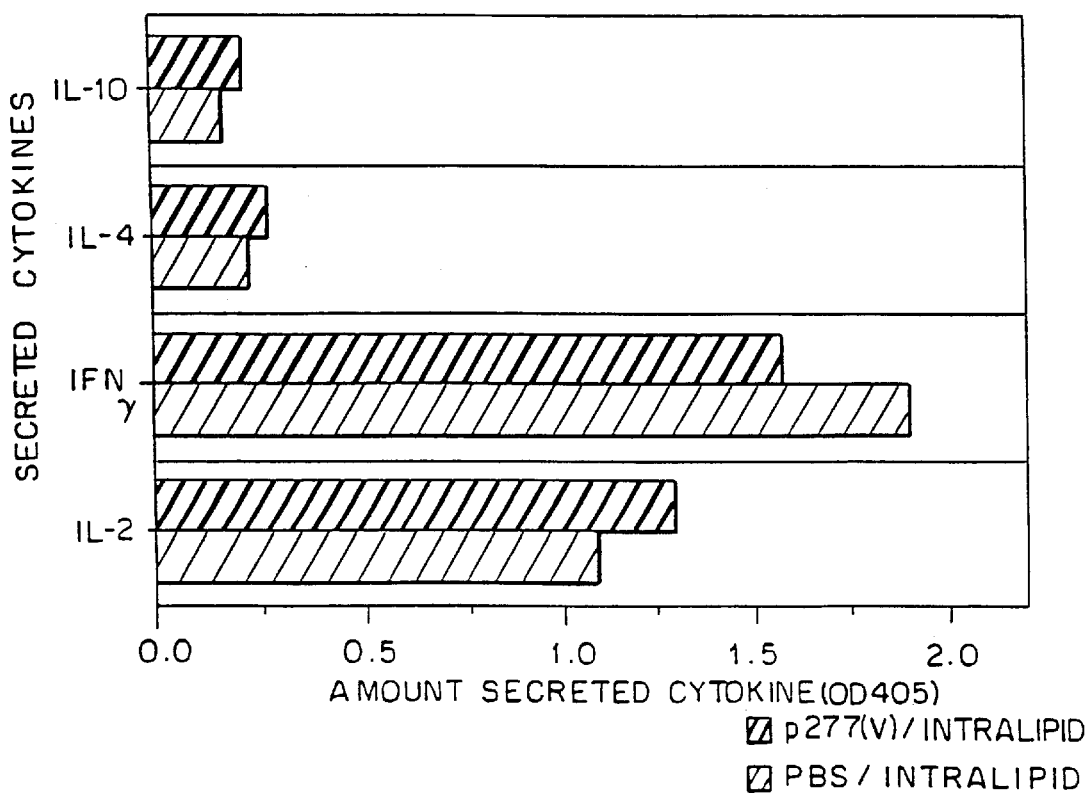

Groups of 10 NOD mice, 3 months old, were treated with p277 in Intralipid or with PBS in Intralipid (see Example 1). Five weeks later, the spleens of the mice were removed and the spleen cells were pooled. The spleen cells were incubated with Con A or p277 for 24 h (for IL-2 and IL-4 secretion) or for 48 h (for IL-10 and IFNγ secretion). The presence of the cytokines in the culture supernatants was quantitated by ELISA, using Pharmingen paired antibodies according to the Pharmingen cytokine ELISA protocol. Pharmingen recombinant mouse cytokines were used as standards for calibration curves. Briefly, flat-bottom 96-well microtiter plates were coated with rat anti-mouse cytokine mAbs for 18 h at 4° C., and the culture supernatants or recombinant mouse cytokines were added for 18 h at 4° C. The plates were washed, and biotinylated rat anti-mouse cytokine mAbs were added for 45 min at room temperature, then extensively washed, and avidin-alkaline phosphatase was added. The plates were washed, a chromogen substrate was added and samples were read at 405 nm in an ELISA reader. The results are shown in FIGS. 5A–B. The concentrations of cytokines are shown as the OD readings.

FIG. 5A shows that the spleen cells of control mice secreted both IL-2 and IFNγ upon incubation with p277. In contrast, the p277-treated mice produced significantly less ($p<0.01$) IL-2 and IFNγ in response to incubation with peptide p277. This reduction in TH1 cytokines was specific; the p277-treated mice maintained their IL-2 and IFNγ cytokine responses to Con A (FIG. 5B). FIGS. 5A and 5B show the amounts of IL-10 and IL-4 produced by the spleen cells of the mice. The control mice produced very little IL-4 or IL-10 in response to p277 or Con A. In contrast, there was a significant increase in IL-10 and IL-4 in response only to p277 and only in the p277/Intralipid-treated mice ($p<0.01$). A decrease in IL-2 and IFNγ coupled with an increase in IL-10 and IL-4 confirms the shift from TH1-like behavior to TH2-like behavior.

All references cited herein, including journal articles or abstracts, published or corresponding U.S. or foreign patent applications, issued U.S. or foreign patents, or any other references, are entirely incorporated by reference herein, including all data, tables, figures, and text presented in the cited references. Additionally, the entire contents of the references cited within the references cited herein are also entirely incorporated by reference.

Reference to known method steps, conventional method steps, known methods or conventional methods is not in any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

REFERENCES

1. Bach, J-F. Curr Opin. Immunol., 3, 902–905 (1991).
2. Harrison, L. C. Immunology Today, 13, 348–52 (1992).
3. Kaufman D. L. et al. Nature 336:69–72 (1993).
4. Tisch, R., Yand, X. D., Singer, S. M., Liblau, R. S., Fugger, L. & McDevitt, H. O. Nature, 366, 72–75 (1993).
5. Bowman, M. A., Leiter, E. H. & Atkinson, M. A. Immunology Today, 15, 115–20 (1994).
6. Elias, D., Reshef, T., Birk, O. S., van der Zee, R., Walker, M. D. & Cohen, I. R. Proc. Natl. Acad. Sci. USA, 88, 3088–91 (1991).
7. Elias, D. & Cohen, I. R. Lancet, 343, 704–706 (1994).
8. Mueller, D. L., Jenkins, M. K. & Schwartz, R. H. Ann. Rev. Immunol., 7, 445–480 (1989).
9. Elias, D., Markovits, D., Reshef, T., van der Zee, R. & Cohen, I. R. Proc. Natl., Acad. Sci. USA 87, 1576–1580 (1990).
10. Mosmann, T. R. & Coffman, R. L. Ann. Rev. Immunol., 7, 145–173 (1989).
11. Banchereau, J., & Rybak, M. E. (1994) "Interleukin 4" in the Cytokine Handbook 2nd ed., A. Thompson, Ed. Academic Press, New York, pp.99.
12. Moore, K. V., O'Garra, A., de Waal Malefyt, R., Vieira, P. & Mosmann, T. R. Ann. Rev. Immunol., 11, 165–190 (1993).
13. Snapper, C. M,. & Mond, J. J. Immunology Today, 14, 15–17 (1993).
14. Snapper, C. M., Waegell W, Beernink, H. & Dasch, J. R. J. Immunol., 151, 4625–36 (1993).
15. Cohen, I. R. Chem. Immunol. 60, 150–60 (1995).
16. Liblau, R. S., Singer, S. M. & McDevitt, H. O. Immunology Today, 16, 34–38 (1995).
17. Romagnani, S. Annu. Rev. Immunol. 12:227–57 (1994).
18. Pennline K. J., Roque-Gaffney, E. & Monahan, M., Clin. Immunol. Immunopathol., 71,169–75 (1994).
19. Rapoport, M. J. et al. J. Exp. Med. 178, 87–99 (1993).
20. Rabinovitch, A., Suarez-Pinzon, W. K., Sorensen, O., Bleakley, R. C., Power, R. F. & Rajotte, R. V. Tranplantation, in press.
21. Shehadeh, N., LaRosa, F. & Lafferty. K. J. J. Autoimmunity, 6, 291–300 (1993).
22. Rabinovitch, A., Sorensen, O., Suarez-Pinzon, W. K., Rajotte, R. V. & Bleakley, R. C. Diabetologia, 37,833–37 (1994).
23. Elliott, J. F. et al. Diabetes, 43,1494–99 (1994).
24. Weiner, H. L. et al. Annu. Rev. Immunol. 12,809–837 (1994).
25. Cohen, I. R. Immunol. Today, 13,490–494 (1992).

What is claimed is,:

1. A method for detecting or monitoring the efficacy of treatment of insulin-dependent diabetes mellitus (IDDM) in an animal by administration of a vaccine comprising a peptide of the 60 kDa heat shock protein auto-antigen in a tolerogenic carrier, the method comprising:

measuring, prior to treatment, the nature of the cytokine response of T cells from the animal to be treated elicited by in vitro incubation of said T cells with the auto-antigen;

measuring, after treatment, the nature of the cytokine response of T cells from the treated animal elicited by in vitro incubation of said T cells with the auto-antigen;

determining whether there has been a shift from a TH1 T cell response prior to treatment to a TH2 T cell response after treatment; and concluding that there is the probability that the treatment has been effective if a positive finding of such a shift is determined in said determining step.

2. A method in accordance with claim 1, wherein said auto-antigen is the p277 peptide auto-antigen.

3. A method in accordance with claim 2, wherein said p277 peptide auto-antigen is that having the sequence of SEQ ID NO:3.

* * * * *

UNITED STATES PATENT AND TRADEMARK OFFICE
CERTIFICATE OF CORRECTION

PATENT NO.    : 6,309,847 B1
DATED         : October 30, 2001
INVENTOR(S)   : Cohen et al.

It is certified that error appears in the above-identified patent and that said Letters Patent is hereby corrected as shown below:

<u>Title page,</u>
At "[86], § 371 Date": change "Jul. 22, 1996" to -- Jul. 22, 1998 --; and
At "[86], § 102 (e) Date": change "Jul. 22, 1996" to -- Jul. 22, 1998 --.
At "[56], References Cited", insert:
-- FOREIGN PATENT DOCUMENTS
   96/06630     07/1996     (WO) --.

Under the heading "OTHER PUBLICATIONS", add the following references:
--Snapper, C.M. et al., "Towards a comprehensive view of immunoglobulin class switching", Immunology Today, vol. 14, no. 1, pp. 16-17 (1993). --

-- Khoury, S.J. et al., Oral tolerance to myelin basic protein and natural recovery from experimental autoimmune encephalomyelitis are associated with downregulation of inflammatory cytokines and differential upregulation of transforming growth factor β, interleukin 4, and prostaglandin E expression in the brain", Journal of Experimental Medicine, vol. 176, pp. 1355-1364 (1992). --.

Signed and Sealed this

Ninth Day of April, 2002

*Attest:*

JAMES E. ROGAN
*Attesting Officer*       *Director of the United States Patent and Trademark Office*

SEQUENCE LISTING (1) GENERAL INFORMATION:

(iii) NUMBER OF SEQUENCES: 3

(2) INFORMATION FOR SEQ ID NO: 1:

(i) SEQUENCE CHARACTERISTICS:
      (A) LENGTH: 20 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO: 1:

Ile Pro Pro Ser Leu Arg Thr Leu Glu Asp Asn Glu Glu Arg Met Ser
1               5                   10                  15

Arg Leu Ser Lys
            20

(2) INFORMATION FOR SEQ ID NO: 2:

```
    (i) SEQUENCE CHARACTERISTICS:
        (A) LENGTH: 17 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 2:

Glu Gly Asp Glu Ala Thr Gly Ala Asn Ile Val Lys Val Ala Leu Glu
1               5                  10                  15

Ala (2) INFORMATION FOR SEQ ID NO: 3:

(i) SEQUENCE CHARACTERISTICS:
        (A) LENGTH: 24 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 3:

Val Leu Gly Gly Gly Val Ala Leu Leu Arg Val Leu Pro Ala Leu Asp
1               5                  10                  15

Ser Leu Thr Pro Ala Asn Glu Asp
                20
```